United States Patent
Allawi et al.

(10) Patent No.: US 10,106,844 B2
(45) Date of Patent: *Oct. 23, 2018

(54) NORMALIZATION OF POLYMERASE ACTIVITY

(71) Applicant: EXACT SCIENCES DEVELOPMENT COMPANY, LLC, Madison, WI (US)

(72) Inventors: Hatim Allawi, Middleton, WI (US); Rebecca Oldham-Haltom, Marshall, WI (US); Zubin Gagrat, Madison, WI (US); Michael Domanico, Middleton, WI (US); Graham Lidgard, Madison, WI (US)

(73) Assignee: Exact Sciences Development Company, LLC, Madison, WI (US)

( * ) Notice: Subject to any disclaimer, the term of this patent is extended or adjusted under 35 U.S.C. 154(b) by 204 days.

This patent is subject to a terminal disclaimer.

(21) Appl. No.: 14/939,651

(22) Filed: Nov. 12, 2015

(65) Prior Publication Data

US 2016/0060683 A1    Mar. 3, 2016

Related U.S. Application Data

(63) Continuation of application No. 14/036,649, filed on Sep. 25, 2013, now Pat. No. 9,212,392.

(60) Provisional application No. 61/705,603, filed on Sep. 25, 2012.

(51) Int. Cl.
C12Q 1/68      (2018.01)
C12P 19/34     (2006.01)
C12Q 1/686     (2018.01)
C12Q 1/6851    (2018.01)

(52) U.S. Cl.
CPC ........... *C12Q 1/686* (2013.01); *C12Q 1/6851* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,432,272 A | 7/1995 | Benner et al. |
| 5,494,810 A | 2/1996 | Barany et al. |
| 5,508,169 A | 4/1996 | Deugau et al. |
| 5,587,287 A | 12/1996 | Scalice et al. |
| 5,624,802 A | 4/1997 | Urdea et al. |
| 5,639,611 A | 6/1997 | Wallace et al. |
| 5,660,988 A | 8/1997 | Burnaby et al. |
| 5,677,152 A | 10/1997 | Birch et al. |
| 5,693,502 A | 12/1997 | Gold et al. |
| 5,710,264 A | 1/1998 | Urdea et al. |
| 5,773,258 A | 6/1998 | Birch et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short et al. |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade et al. |
| 6,020,130 A | 2/2000 | Gold et al. |
| 6,063,573 A | 5/2000 | Kayyem et al. |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Corsette et al. |
| 6,150,097 A | 11/2000 | Tyagi et al. |
| 6,150,510 A | 11/2000 | Seela et al. |
| 6,183,960 B1 | 2/2001 | Lizardi et al. |
| 6,210,884 B1 | 4/2001 | Lizardi et al. |
| 6,221,583 B1 | 4/2001 | Kayyem et al. |
| 6,235,502 B1 | 5/2001 | Weissman et al. |
| 6,248,229 B1 | 6/2001 | Meade et al. |

(Continued)

FOREIGN PATENT DOCUMENTS

| | | |
|---|---|---|
| WO | WO1992/002258 | 2/1992 |
| WO | WO1993/10820 | 6/1993 |
| WO | WO1994/22892 | 10/1994 |
| WO | WO1994/24144 | 10/1994 |
| WO | WO2002/070755 | 9/2002 |
| WO | WO2005/023091 | 3/2005 |
| WO | WO 2005042713 | 5/2005 |
| WO | WO 2005086938 | 9/2005 |
| WO | WO2012/155072 | 11/2012 |

OTHER PUBLICATIONS

Barany, "The ligase chain reaction in a PCR world," Genome Research, vol. 1, pp. 5-16. (Year: 1991).*
Ballabio, et al., "Screening for steroid sulfatase (STS) gene deletions by multiplex DNA amplification," Human Genetics, 1990, 84(6) 571-573.
Barany, "Genetic disease detection and DNA amplification using cloned thermostable ligase," Proc. Natl. Acad. Sci USA, 1991, 88, 189-93.

(Continued)

*Primary Examiner* — Young J Kim
(74) *Attorney, Agent, or Firm* — Casimir Jones, S.C.; Mary Ann D. Brow

(57) ABSTRACT

Provided herein is technology relating to the amplification-based detection of nucleic acids and particularly, but not exclusively, to methods and compositions for minimizing variability in the activity between different samples or manufacturing lots of DNA polymerases, such as Taq DNA polymerase.

7 Claims, 8 Drawing Sheets

(56) References Cited

U.S. PATENT DOCUMENTS

| | | | |
|---|---|---|---|
| 6,329,178 | B1 | 12/2001 | Patel et al. |
| 6,395,524 | B2 | 5/2002 | Loeb et al. |
| 6,602,695 | B2 | 8/2003 | Patel et al. |
| 6,872,816 | B1 | 3/2005 | Hall et al. |
| 7,662,594 | B2 | 2/2010 | Kong et al. |
| 8,361,720 | B2 | 1/2013 | Oldham-Haltom et al. |
| 9,212,392 | B2 * | 12/2015 | Allawi .................... C12Q 1/686 |
| 2005/0186588 | A1 | 8/2005 | Lyamichev et al. |
| 2006/0147955 | A1 | 7/2006 | Allawi et al. |
| 2007/0048748 | A1 | 3/2007 | Williams et al. |
| 2007/0202525 | A1 | 8/2007 | Quake et al. |
| 2009/0253142 | A1 | 10/2009 | Allawi et al. |
| 2012/0122088 | A1 | 5/2012 | Zou et al. |
| 2012/0122106 | A1 | 5/2012 | Zou et al. |
| 2013/0231256 | A1 | 9/2013 | Oldham-Haltom et al. |

OTHER PUBLICATIONS

Bustin, "Absolute quantification of mRNA using real-time reverse transcription polymerase chain reaction assays," J. Molecular Endocrinology, 2000, 25:169-193.

Chamberlain et al. "Deletion screening of the Duchenne muscular dystrophy locus via multiplex DNA Amplification," Nucleic Acids Research, 1988, 16(23) 11141-11156.

Coyne et al., Improved quantitative real-time PCR assays for enumeration of harmful *algal* species in field samples using an exogenous DNA reference standard, Limnology and Oceanography: Methods, 3(9):381-391.

Don et al., "Touchdown PCR to circumvent spurious priming during gene amplification," Nucleic Acids Research, 1991, 19(14):4008.

Ellison et al., "Routes to improving the reliability of low level DNA analysis using real-time PCR," BMC Biotechnology, 2006, 6:33.

Fasman, "Practical Handbook of Biochemistry and Molecular Biology," CRC Press, Inc., 1989, pp. 385-394.

Guescini et al., "A new real-time PCR method to overcome significant quantitative inaccuracy due to slight amplification inhibition," BMC Bioinformatics, 2008, 9:326.

Guilfoyle et al., "Ligation-mediated PCR amplification of specific fragments from Class-11 restriction endonuclease total digests," Nucleic Acids Research, 1997, 25(9):1854-1858.

Hall et al., "Sensitive detection of DNA polymorphisms by the serial invasive signal amplification reaction," PNAS, USA, 2000, 97(15):8272.

Hayden et al., "Multiplex-Ready PCR: A new method for multiplexed SSR and SNP genotyping," BMC Genomics, 2008, 9:80.

Hecker et al., "High and Low Annealing Temperatures Increase Both Specificity and Yield in Touchdown and Stepdown PCR," Biotechniques, 1996, 20(3) 478-485.

Herman et al., "Methylation-specific PCR: A novel PCR assay for methylation status of CpG islands," PNAS, USA, 1996, 93(13): 9821-9826.

Higuchi et al., "A general method of in vitro preparation and specific mutagenesis of DNA fragments: study of protein and DNA interactions," Nucleic Acids Research, 1988, 16(15): 7351-7367.

Higuchi et al., "Kinetic PCR Analysis: Real-time Monitoring of DNA Amplification Reactions," Biotechnology, 1993, 11:1026-1030.

Higuchi et al., "Simultaneous amplification and detection of specific DNA sequences," Biotechnology, 1992, 10:413-417.

Hoebeeck et al., "Real-Time PCR Quality Control for Gene Expression Profiling Using the LightCycler 480 System," Biochemica, 2007, No. 2.

Hussy et al., "Quantitative Fluorogenic PCR Assay for Measuring Ovine Herpesvirus 2 Replication in Sheep," Clinical and Diagnostic Laboratory Immunology, 2001, 8(1):123-128.

Kaboev et al., "PCR hot start using primers with the structure of molecular beacons (hairpin-like structure)," Nucleic Acids Research, 2000, 28(21): 1-2.

Kaiser et al., "A Comparison of Eubacterial and Archaeal Structure-specific 5'—Exonucleases," The Journal Biol. Chem., 1999, 274:21387.

Kalinina et al., "Nanoliter scale PCR with TaqMan detection," Nucleic Acids Research, 1997, 25; 1999-2004.

Lyamichev et al., "Polymorphism identification and quantitative detection of genomic DNA by invasive cleavage of oligonucleotide probes," Nature Biotech., 1999, 17:292.

Olivier, "The Invader assay for SNP genotyping," Mutation Research, 2005, 573, 103-110.

Orpana, "Fluorescence resonance energy transfer (FRET) using ssDNA binding fluorescent dye," Biomol Eng, 2004, 21, 45-50.

Roux et al., "Polythiophene Derivatives: Smart Materials," Biotechniques, 1994, 16(5) 812-814.

Rutledge and Stewart. "Critical evaluation of methods used to determine amplification efficiency refutes the exponential character of real-time PCR." BMC Molecular Biology, 2008. 9:96.

Schouten et al. "Relative quantification of 40 nucleic acid sequences by multiplex ligation-dependent probe amplification," Nucleic Acids Research, 2002, 30(12): e57.

Selvin, "Fluorescence Resonance Energy Transfer," Methods Enzymol., 1995, 246:300.

Shen et al., "Multiple but dissectible functions of FEN-1 nucleases in nucleic acid processing, genome stability and diseases," BioEssays, 2005, 27(7):717-729.

Spackman et al., Development of a real-time reverse transcriptase PCR assay for type A influenza virus and the avian H5 and H7 hemagglutinin subtypes, J Clin Microbiol. Sep. 2002;40(9):3256-60.

Stryer, "Fluorescence Energy Transfer as a Spectroscopic Ruler," Ann. Rev. Biochem., 1978, 47:819-46.

Triglia et al., "A procedure for in vitro amplification of DNA segments that lie outside the boundaries of known sequences," Nucleic Acids Res., 1988, 16:8186.

Vogelstein and Kinzler, "Digital PCR," Proc Natl Acad Sci USA, 1999, 96:9236-41.

Zou et al., "Quantification of Methylated Markers with a Multiplex Methylation-Specific Technology", Clinical Chemistry, 2012, 58: 2.

Ahlquist et al. Next-generation stool DNA test accurately detects colorectal cancer and large adenomas. Gastroenterology. Feb. 2012;142(2):248-56.

Exact Sciences Corp., Cologuard Physician Brochure. Oct. 29, 2010, 14 pages.

Google Search for Cologuard Physician Brochure. Performed Jun. 26, 2017, 1 page.

European Search Report for EP14872569.0, dated Jul. 18, 2017, 14 pages.

* cited by examiner

NORMALIZATION OF POLYMERASE ACTIVITY

CROSS-REFERENCE TO RELATED APPLICATIONS

The present application is a continuation U.S. patent application Ser. No. 14/036,649 filed Sep. 25, 2013 claims the benefit of U.S. Provisional Patent Application 61/705,603, filed Sep. 25, 2012, each of which is incorporated by reference in its entirety.

FIELD OF THE INVENTION

Provided herein is technology relating to the amplification-based detection of nucleic acids and particularly, but not exclusively, to methods and compositions for altering the behavior of calibration standards to mimic natural samples and minimize variability in the activity of manufactured polymerases such as Taq DNA polymerase.

BACKGROUND

Methods for the quantification of nucleic acids are important in many areas of molecular biology and in particular for molecular diagnostics. At the DNA level such methods are used, for example, to determine the copy numbers of gene sequences amplified in the genome. Further, methods for the quantification of nucleic acids are used to determine mRNA quantities as a measure of gene expression.

Among the number of different analytical methods that detect and quantify nucleic acids or nucleic acid sequences, variants of the polymerase chain reaction (PCR) have become the most powerful and widespread technology, the principles of which are disclosed in U.S. Pat. Nos. 4,683,195; 4,683,202; and 4,965,188. Automated methods of amplification typically rely on the use of thermostable DNA polymerases, e.g., from *Thermus aquaticus* and other thermophilic organisms, or engineered by truncation, modification, or chimerization of proteins from thermophilic organisms. Accordingly, many manufacturers now produce thermostable polymerases from a variety of sources. For example, the DNA polymerase I from *Thermus aquaticus* ("Taq" polymerase) is produced by a number of different manufacturers and one concern is the variability in the activity of such enzymes between the producers of the enzyme, and/or between different lots of enzyme from a single producer.

In order to minimize the consequences of spurious reactions at temperatures below the optimal PCR conditions, such as during reaction set up, a number of methods have been developed for suppressing the activity of the Taq polymerase prior to the desired start of the reaction, known collectively as "hot start PCR" or "hot start Taq." These include chemical modification of the Taq (U.S. Pat. Nos. 5,677,152 and 5,773,258), binding antibody to the Taq enzyme (U.S. Pat. Nos. 5,338,671 and 5,587,287), and aptamer binding to the Taq (U.S. Pat. Nos. 5,693,502 and 6,020,130, as well as others methods of hot start. One of the practical consequences of hot start technology is that assaying and adjusting the activity of the Taq enzyme becomes technically more challenging for Taq enzyme vendors.

In addition, the maturation of PCR and related amplification techniques has produced powerful technologies to detect nucleic acids with increasing accuracy and precision. These techniques require that variability in the activity of polymerase be minimal, not only as it varies between suppliers but also as it varies among lots of a single supplier's production runs. As such, minimizing the variability of polymerase activity in nucleic acid detection reactions is a problem for some amplification methods.

SUMMARY

In the course of development of methods described herein, it has been determined that different preparations of enzymes, e.g., different manufacturing lots of Taq polymerase from the same vendor, have produced different results as judged by variation in the standard curves generated for quantitative analysis. For example, during the development of a quantitative allele-specific real-time target and signal amplification (QuARTS) assay (see, e.g., U.S. Pat. Appl. Pub. No. 2009/0253142 or U.S. Pat. No. 8,361,720), using combined target amplification and FEN-1-mediated signal amplification, and related to detecting nucleic acids associated with colon cancer, such variation was manifested as an observed difference in the slopes and/or intercepts of the standard curves that changed as a function of Taq polymerase manufacturing lot. In these types of assays, standard curves are used to quantify the number of target DNAs in the assay sample; thus, variations in the standard curves may produce errors in the copy number calculated for the particular DNA that is evaluated by the test. Surprisingly, the lot-to lot variability of the polymerase enzyme could not be compensated for by adjusting the amounts of polymerase added to the reactions.

Accordingly, provided herein is technology related to a method for minimizing enzyme variability in an assay sample or reaction mixture comprising a target nucleic acid a DNA polymerase, a flap endonuclease, and a hairpin oligonucleotide, the method comprising adding purified, exogenous, non-target nucleic acid, e.g., DNA, to the reaction mixture; and measuring the amount of the target nucleic acid in the reaction mixture. In preferred embodiments, the reaction mixture further comprises a primer. In certain particularly preferred embodiments, the hairpin oligonucleotide comprises a FRET cassette oligonucleotide. In certain embodiments, the target nucleic acid is human. In preferred embodiments, the target nucleic acid is DNA.

In some embodiments, purified non-target DNA included in the assay reaction mixture is isolated from fish, e.g., herring, cod, and/or salmon. In some preferred embodiments, the non-target DNA is a mixture of DNA isolated from different sources. For example, in some embodiments the DNA is isolated from two or more different kinds of fish, e.g., a mixture of fish such as herring, cod, and/or salmon. Embodiments also provide non-target nucleic acid isolated from mammals, fish, birds, amphibians, etc. In some embodiments, the non-target DNA comprises DNA isolated from mouse.

In some embodiments, the non-target nucleic acid is added at a concentration of approximately 2 to approximately 20 nanograms per µl of the reaction mixture. In certain embodiments, the non-target nucleic acid is added at a concentration of approximately 6 to 7 nanograms per µl of reaction mixture volume.

In some embodiments, the target nucleic acid is a calibrator or a standard, e.g., in a dilution series for quantitative amplification reactions. In some embodiments, measuring the amount of the target nucleic acid in the reaction mixture comprises use of a PCR-invasive cleavage assay, such as a QuARTS assay. In some embodiments, the target nucleic acid is a human nucleic acid, e.g., in some embodiments, human DNA. Furthermore, some embodiments provide that the target nucleic acid comprises human genomic DNA.

In another aspect, the technology relates to a composition comprising human genomic DNA; an oligonucleotide specific for the human genomic DNA; a DNA polymerase; a flap endonuclease; a FRET cassette, and purified exogenous non-target DNA. In some embodiments the polymerase is Taq polymerase. In some embodiments, the extraneous, non-target DNA is isolated from fish.

In some embodiments of the technology, the DNA polymerase used comprises a thermostable DNA polymerase. In certain embodiments, the thermostable DNA polymerase is a eubacterial DNA polymerase, and in some preferred embodiments, the eubacterial DNA polymerase is Taq DNA polymerase, i.e., is isolated from *Thermus aquaticus*. In certain preferred embodiments, the DNA polymerase is modified for hot start PCR.

In some embodiments, the flap endonuclease used comprises a FEN-1 endonuclease, and in certain embodiments, said FEN-1 endonuclease is from an archaeal organism. In particularly preferred embodiments, the flap endonuclease is thermostable.

The technology also provides reaction mixtures configured for minimizing enzyme variability in performance of an assay. In some embodiments, reaction mixtures of the technology comprise target nucleic acid; purified exogenous non-target DNA, and PCR-invasive cleavage assay reagents comprising, e.g., thermostable DNA polymerase, dNTPs; a first primer and a second primer configured for amplifying a product from the target nucleic acid; a flap endonuclease, a FRET cassette, and a flap oligonucleotide, wherein the reaction mixture is characterized in that it can amplify the target nucleic acid and produce a detectable signal proportional to the amount of target nucleic acid in the mixture.

In some configurations, the technology provides a set of reaction mixtures, each of said reaction mixtures in the set comprising PCR-invasive cleavage assay reagents comprising thermostable DNA polymerase; dNTPs; a first primer and a second primer configured for amplifying a product from said target nucleic acid; a flap endonuclease, a FRET cassette, and a flap oligonucleotide. In certain embodiments, each reaction mixture in the set of reaction mixtures is characterized in that it can amplify the target nucleic acid and produce a detectable signal proportional to the amount of said target nucleic acid in that reaction mixture. In preferred embodiments, the set of reaction mixtures comprises a dilution series in which each member of the dilution series comprises a different known amount of the target nucleic acid, and essentially the same concentrations of the components of the PCR-invasive cleavage assay reagents.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1:
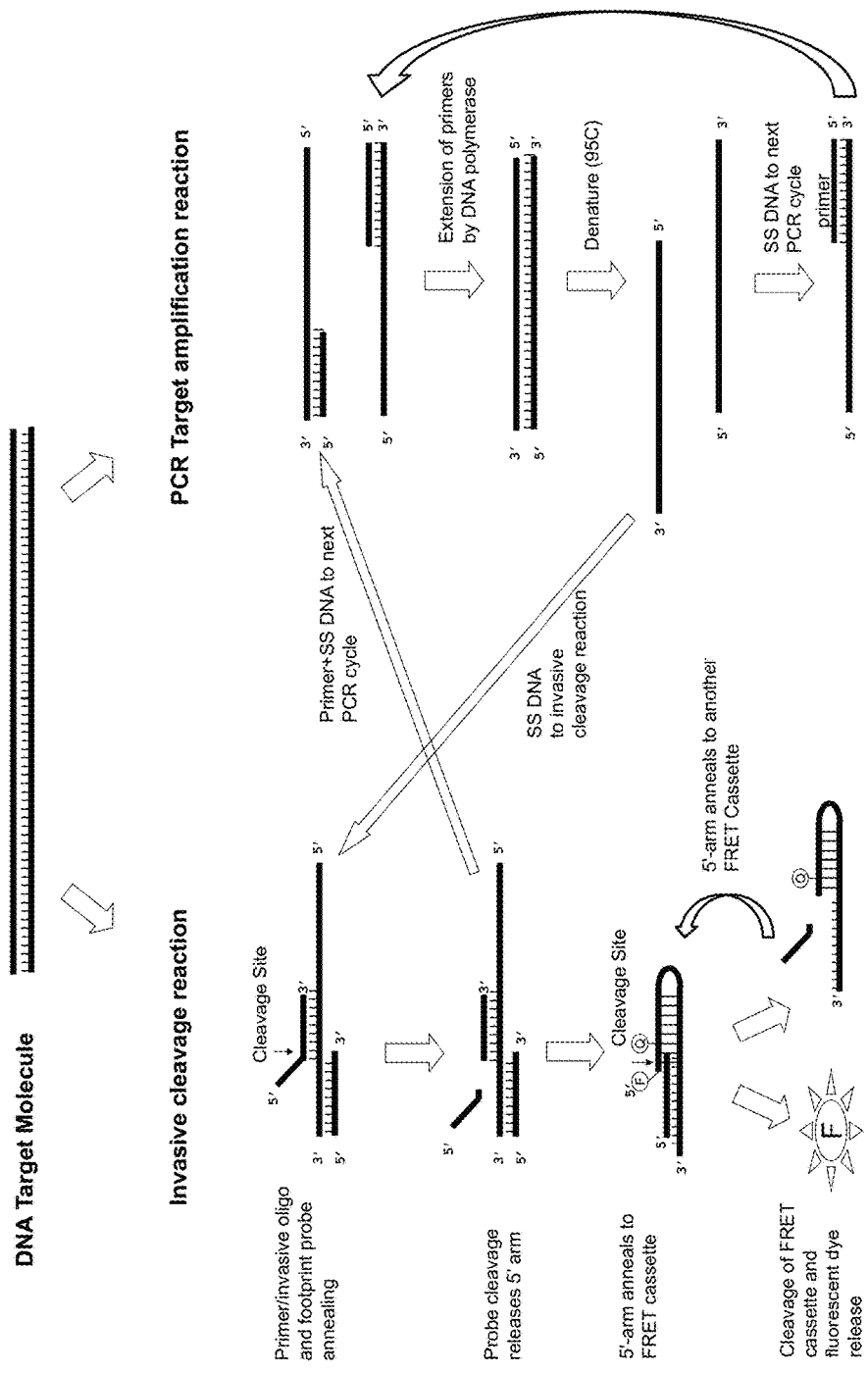
FIG. 1 provides a schematic diagram of a combined PCR-invasive cleavage assay.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein in reference to non-target DNA, the term "exogenous" refers to non-target DNA that is isolated and purified from a source other than the source or sample containing the target DNA. For example, purified fish DNA is exogenous DNA with respect to a sample comprising human target DNA. Exogenous DNA need not be from a different organism than the target DNA. For example, purified fish DNA obtained commercially would be exogenous if added to a reaction configured to detect a target nucleic acid in a sample from a particular fish. In preferred embodiments, exogenous DNA is selected to be undetected by an assay configured to detect and/or quantify the target nucleic acid in the reaction in to which the exogenous DNA is added.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically. In some embodiments, an oligonucleotide primer is used with a template nucleic acid and extension of the primer is template dependent, such that a complement of the template is formed.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al., (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the "INVADER" flap assay, or invasive cleavage assay, (Hologic, Inc.) described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and in combined PCR/invasive cleavage assays (Hologic, Inc., e.g., in U.S. Patent Publications 2006/0147955 and 2009/0253142), each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barany Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication 20090253142 A1 (application. Ser. No. 12/404,240), incorporated herein by reference in its entirety for all purposes, and as diagrammed in FIG. 1. Because many copies of the FRET cassette are cleaved for each copy of the target amplicon produced, the assay is said to produce "signal amplification" in addition to target amplification. Additional amplification plus invasive cleavage detection configurations, termed the QuARTS method, are described in U.S. Pat. No. 8,361,720, and in U.S. patent application Ser. Nos. 12/946,745; and 12/946,752, incorporated herein by reference in their entireties for all purposes.

As used herein, the term "PCR-invasive cleavage assay" refers to an assay in which target nucleic acid is amplified and amplified nucleic acid is detected simultaneously using a signal-amplifying invasive cleavage assay employing a FRET cassette, and in which the assay reagents comprise a mixture containing DNA polymerase, FEN-1 endonuclease, a primary probe comprising a portion complementary to a target nucleic acid, and a hairpin FRET cassette. PCR-invasive cleavage assays include the QuARTS assays described in U.S. Pat. No. 8,361,720, and in U.S. patent application Ser. Nos. 12/946,745; and 12/946,752, and the amplification assays of US Patent Publication 20090253142 A1 as diagrammed in FIG. 1.

As used herein, the term "PCR-invasive cleavage assay reagents" refers to one or more reagents for detecting target sequences in a PCR-invasive cleavage assay, the reagents comprising nucleic acid molecules capable of participating in amplification of a target nucleic acid and in formation of an invasive cleavage structure in the presence of the target sequence, in a mixture containing DNA polymerase, FEN-1 endonuclease and a FRET cassette.

As used herein, the term "FRET cassette" refers to a hairpin oligonucleotide that contains a fluorophore moiety and a nearby quencher moiety that quenches the fluorophore. Hybridization of a cleaved flap (e.g., from cleavage of a target-specific probe in a PCR-invasive cleavage assay) with a FRET cassette produces a secondary substrate for the flap endonuclease, e.g., a FEN-1 enzyme. Once this substrate is formed, the 5' fluorophore-containing base is cleaved from the cassette, thereby generating a fluorescence signal. In preferred embodiments, a FRET cassette comprises an unpaired 3' portion to which a cleavage product, e.g., a portion of a cleaved flap oligonucleotide, can hybridize to from an invasive cleavage structure cleavable by a FEN-1 endonuclease.

A nucleic acid "hairpin" as used herein refers to a region of a single-stranded nucleic acid that contains a duplex (i.e., base-paired) stem and a loop, formed when the nucleic acid comprises two portions that are sufficiently complementary to each other to form a plurality of consecutive base pairs.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor flurophore to a non-fluorescing molecule (e.g., a quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "FEN-1" in reference to an enzyme refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "FEN-1 activity" refers to any enzymatic activity of a FEN-1 enzyme, including but not limited to flap endonuclease (FEN), nick exonuclease (EXO), and gap endonuclease (GEN) activities (see, e.g., Shen, et al., BioEssays Volume 27, Issue 7, Pages 717-729, incorporated herein by reference).

As used herein, the term "primer annealing" refers to conditions that permit oligonucleotide primers to hybridize to template nucleic acid strands. Conditions for primer annealing vary with the length and sequence of the primer and are generally based upon the $T_m$ that is determined or calculated for the primer. For example, an annealing step in an amplification method that involves thermocycling involves reducing the temperature after a heat denaturation step to a temperature based on the $T_m$ of the primer sequence, for a time sufficient to permit such annealing.

As used herein, the term "amplifiable nucleic acid" is used in reference to nucleic acids that may be amplified by any amplification method. It is contemplated that "amplifiable nucleic acid" will usually comprise "sample template."

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the terms "reverse transcription" and "reverse transcribe" refer to the use of a template-dependent polymerase to produce a DNA strand complementary to an RNA template.

As used herein, the term "abundance of nucleic acid" refers to the amount of a particular target nucleic acid sequence present in a sample or aliquot. The amount is generally referred to in terms of mass (e.g., µg), mass per unit of volume (e.g., µg/µl); copy number (e.g., 1000 copies, 1 attomole), or copy number per unit of volume (e.g., 1000 copies per ml, 1 attomole per µl). Abundance of a nucleic acid can also be expressed as an amount relative to the amount of a standard of known concentration or copy number. Measurement of abundance of a nucleic acid may be on any basis understood by those of skill in the art as being a suitable quantitative representation of nucleic acid abundance, including physical density or the sample, optical density, refractive property, staining properties, or on the basis of the intensity of a detectable label, e.g. a fluorescent label.

The term "amplicon" or "amplified product" refers to a segment of nucleic acid, generally DNA, generated by an amplification process such as the PCR process. The terms are also used in reference to RNA segments produced by amplification methods that employ RNA polymerases, such as NASBA, TMA, etc.

The term "amplification plot" as used in reference to a thermal cycling amplification reaction refers to the plot of signal that is indicative of amplification, e.g., fluorescence signal, versus cycle number. When used in reference to a non-thermal cycling amplification method, an amplification plot generally refers to a plot of the accumulation of signal as a function of time.

The term "baseline" as used in reference to an amplification plot refers to the detected signal coming from assembled amplification reactions at prior to incubation or, in the case of PCR, in the initial cycles, in which there is little change in signal.

The term "$C_t$" or "threshold cycle" as used herein in reference to real time detection during an amplification reaction that is thermal cycled refers to the fractional cycle number at which the detected signal (e.g., fluorescence) passes the fixed threshold.

The term "no template control" and "no target control" (or "NTC") as used herein in reference to a control reaction refers to a reaction or sample that does not contain template or target nucleic acid. It is used to verify amplification quality.

As used herein, the term "sample template" refers to nucleic acid originating from a sample that is analyzed for the presence of "target." In contrast, "background template" is used in reference to nucleic acid other than sample template that may or may not be present in a sample. The presence of background template is most often inadvertent. It may be the result of carryover, or it may be due to the presence of nucleic acid contaminants sought to be purified away from the sample. For example, nucleic acids from organisms other than those to be detected may be present as background in a test sample.

A sample "suspected of containing" a nucleic acid may contain or not contain the target nucleic acid molecule.

As used herein, the term "sample" is used in its broadest sense. For example, in some embodiments, it is meant to include a specimen or culture (e.g., microbiological culture), whereas in other embodiments, it is meant to include both biological and environmental samples (e.g., suspected of comprising a target sequence, gene or template). In some embodiments, a sample may include a specimen of synthetic origin. Samples may be unpurified or may be partially or completely purified or otherwise processed.

The present technology is not limited by the type of biological sample used or analyzed. The present technology is useful with a variety of biological samples including, but are not limited to, tissue (e.g., organ (e.g., heart, liver, brain, lung, stomach, intestine, spleen, kidney, pancreas, and reproductive organs), glandular, skin, and muscle), cell (e.g., blood cell (e.g., lymphocyte or erythrocyte), muscle cell, tumor cell, and skin cell), gas, bodily fluid (e.g., blood or portion thereof, serum, plasma, urine, semen, saliva, etc.), or solid (e.g., stool) samples obtained from a human (e.g., adult, infant, or embryo) or animal (e.g., cattle, poultry, mouse, rat, dog, pig, cat, horse, and the like). In some embodiments, biological samples may be solid food and/or feed products and/or ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc.

Biological samples also include biopsies and tissue sections (e.g., biopsy or section of tumor, growth, rash, infection, or paraffin-embedded sections), medical or hospital samples (e.g., including, but not limited to, blood samples, saliva, buccal swab, cerebrospinal fluid, pleural fluid, milk, colostrum, lymph, sputum, vomitus, bile, semen, oocytes, cervical cells, amniotic fluid, urine, stool, hair, and sweat), laboratory samples (e.g., subcellular fractions), and forensic samples (e.g., blood or tissue (e.g., spatter or residue), hair and skin cells containing nucleic acids), and archeological samples (e.g., fossilized organisms, tissue, or cells).

Environmental samples include, but are not limited to, environmental material such as surface matter, soil, water (e.g., freshwater or seawater), algae, lichens, geological samples, air containing materials containing nucleic acids, crystals, and industrial samples, as well as samples obtained from food and dairy processing instruments, apparatus, equipment, utensils, disposable and non-disposable items.

Samples may be prepared by any desired or suitable method. In some embodiments, nucleic acids are analyzed directly from bodily fluids, stool, or other samples using the methods described in U.S. Pat. Pub. No. 2005/0186588, U.S. patent application Ser. No. 13/470,251, or PCT/US12/37581, each of which is herein incorporated by reference in its entirety for all purposes.

The above described examples are not, however, to be construed as limiting the sample (e.g., suspected of comprising a target sequence, gene or template (e.g., the presence or absence of which can be determined using the compositions and methods of the present technology)) types applicable to the present technology.

The terms "nucleic acid sequence" and "nucleic acid molecule" as used herein refer to an oligonucleotide, nucleotide or polynucleotide, and fragments or portions thereof. The terms encompasses sequences that include analogs of DNA and RNA nucleotides, including those listed above, and also including, but not limited to, 4-acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, and pyrazolo[3,4-d]pyrimidines such as guanine analogue 6 amino 1H-pyrazolo[3,4d]pyrimidin 4(5H) one (ppG or PPG, also Super G) and the adenine analogue 4 amino 1H-pyrazolo[3,4d]pyrimidine (ppA or PPA). The xanthine analogue 1H-pyrazolo[5,4d]pyrimidin 4(5H)-6(7H)-dione (ppX) can also be used. These base analogues, when present in an oligonucleotide, strengthen hybridization and improve mismatch discrimination. All tautomeric forms of naturally-occurring bases, modified bases and base analogues may be included in the oligonucleotide conjugates of the technology. Other modified bases useful in the present technology include 6-amino-3-prop-1-ynyl-5-hydropyrazolo[3,4-d]pyrimidine-4-one, PPPG; 6-amino-3-(3-hydroxyprop-1-ynyl)-5-hydropyrazolo[3,4-d]pyrimidine-4-one, HOPPPG; 6-amino-3-(3-aminoprop-1-ynyl)-5-hydropyrazolo[3,4-d]pyrimidine-4-one, NH2PPPG; 4-amino-3-(prop-1-ynyl)pyrazolo[3,4-d]pyrimidine, PPPA; 4-amino-3-(3-hydroxyprop-1-ynyl)pyrazolo[3,4-d]pyrimidine, HOPPPA; 4-amino-3-(3-aminoprop-1-ynyl)pyrazolo[3,4-d]pyrimidine, $NH_2$ PPPA; 3-prop-1-ynylpyrazolo[3,4-d]pyrimidine-4,6-diamino, $(NH_2)_2$ PPPA; 2-(4,6-diaminopyrazolo[3,4-d]pyrimidin-3-yl)ethyn-1-ol, $(NH_2)_2$ PPPAOH; 3-(2-aminoethynyl)pyrazolo[3,4-d]pyrimidine-4,6-diamine, $(NH_2)_2$ PPPANH$_2$; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, NH$_2$PC; 5-[4-amino-3-(3-methoxyprop-1-ynyl) pyrazol[3,4-d]pyrimidinyl]-2-(hydroxymethyl)oxolan-3-ol, CH$_3$ OPPPA; 6-amino-1-[4-hydroxy-5-(hydroxymethyl) oxolan-2-yl]-3-(3-methoxyprop-1-ynyl)-5-hydropyrazolo[3,4-d]pyrimidin-4-one, CH$_3$ OPPPG; 4, (4,6-Diamino-1H-pyrazolo[3,4-d]pyrimidin-3-yl)-but-3-yn-1-ol, Super A; 6-Amino-3-(4-hydroxy-but-1-ynyl)-1,5-dihydro-pyrazolo [3,4-d]pyrimidin-4-one; 5-(4-hydroxy-but-1-ynyl)-1H-pyrimidine-2,4-dione, Super T; 3-iodo-1H-pyrazolo[3,4-d]pyrimidine-4,6-diamine (($NH_2$)$_2$PPAI); 3-bromo-1H-pyrazolo [3,4-d]pyrimidine-4,6-diamine (($NH_2$)$_2$ PPABr); 3-chloro-1H-pyrazolo[3,4-d]pyrimidine-4,6-diamine (($NH_2$)$_2$ PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl).

A nucleic acid sequence or molecule may be DNA or RNA, of either genomic or synthetic origin, that may be single or double stranded, and represent the sense or anti-sense strand. Thus, nucleic acid sequence may be dsDNA, ssDNA, mixed ssDNA, mixed dsDNA, dsDNA made into ssDNA (e.g., through melting, denaturing, helicases, etc.), A-, B-, or Z-DNA, triple-stranded DNA, RNA, ssRNA, dsRNA, mixed ss and dsRNA, dsRNA made into ssRNA (e.g., via melting, denaturing, helicases, etc.), messenger RNA (mRNA), ribosomal RNA (rRNA), transfer RNA (tRNA), catalytic RNA, snRNA, microRNA, or protein nucleic acid (PNA).

The present technology is not limited by the type or source of nucleic acid (e.g., sequence or molecule (e.g. target sequence and/or oligonucleotide)) utilized. For example, the nucleic acid sequence may be amplified or created sequence (e.g., amplification or creation of nucleic acid sequence via synthesis (e.g., polymerization (e.g., primer extension (e.g., RNA-DNA hybrid primer technology)) and reverse transcription (e.g., of RNA into DNA)) and/or amplification (e.g., polymerase chain reaction (PCR), rolling circle amplification (RCA), nucleic acid sequence based amplification (NASBA), transcription mediated amplification (TMA), ligase chain reaction (LCR), cycling probe technology, Q-beta replicase, strand displacement amplification (SDA), branched-DNA signal amplification (bDNA), hybrid capture, and helicase dependent amplification).

The terms "nucleotide" and "base" are used interchangeably when used in reference to a nucleic acid sequence, unless indicated otherwise herein. A "nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, LO), all herein incorporated by reference in their entireties.

The term "oligonucleotide" as used herein is defined as a molecule comprising two or more nucleotides (e.g., deoxyribonucleotides or ribonucleotides), preferably at least 5 nucleotides, more preferably at least about 10-15 nucleotides and more preferably at least about 15 to 30 nucleotides, or longer (e.g., oligonucleotides are typically less than 200 residues long (e.g., between 15 and 100 nucleotides), however, as used herein, the term is also intended to encompass longer polynucleotide chains). The exact size will depend on many factors, which in turn depend on the ultimate function or use of the oligonucleotide. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes. Oligonucleotides may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. As used herein, the terms "complementary" or "complementarity" are used in reference to polynucleotides (e.g., a sequence of two or more nucleotides (e.g., an oligonucleotide or a target nucleic acid)) related by the base-pairing rules. For example, the sequence "5'-A-G-T-3'," is complementary to the sequence "3'-T-C-A-5'." Complementarity may be "partial," in which only some of the nucleic acid bases are matched according to the base pairing rules. Or, there may be "complete" or "total" complementarity between the nucleic acid bases. The degree of complementarity between nucleic acid strands has significant effects on the efficiency and strength of hybridization between nucleic acid strands. This is of particular importance in amplification reactions, as well as detection methods that depend upon the association of two or more nucleic acid strands. Either term may also be used in reference to individual nucleotides, especially within the context of polynucleotides. For example, a particular nucleotide within an oligonucleotide may be noted for its complementarity, or lack thereof, to a nucleotide within another nucleic acid sequence (e.g., a target sequence), in contrast or comparison to the complementarity between the rest of the oligonucleotide and the nucleic acid sequence.

The complement of a nucleic acid sequence as used herein refers to an oligonucleotide which, when aligned with the nucleic acid sequence such that the 5' end of one sequence is paired with the 3' end of the other, is in "antiparallel association." Nucleotide analogs, as discussed above, may be included in the nucleic acids of the present technology and include. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "label" refers to any moiety (e.g., chemical species) that can be detected or can lead to a detectable response. In some preferred embodiments, detection of a label provides quantifiable information. Labels can be any known detectable moiety, such as, for example, a radioactive label (e.g., radionuclides), a ligand (e.g., biotin or avidin), a chromophore (e.g., a dye or particle that imparts a detectable color), a hapten (e.g., digoxygenin), a mass label, latex beads, metal particles, a paramagnetic label, a luminescent compound (e.g., bioluminescent, phosphorescent or chemiluminescent labels) or a fluorescent compound.

A label may be joined, directly or indirectly, to an oligonucleotide or other biological molecule. Direct labeling can occur through bonds or interactions that link the label to the oligonucleotide, including covalent bonds or non-covalent interactions such as hydrogen bonding, hydrophobic and ionic interactions, or through formation of chelates or coordination complexes. Indirect labeling can occur through use of a bridging moiety or "linker", such as an antibody or additional oligonucleotide(s), which is/are either directly or indirectly labeled.

Labels can be used alone or in combination with moieties that can suppress (e.g., quench), excite, or transfer (e.g., shift) emission spectra (e.g., fluorescence resonance energy transfer (FRET)) of a label (e.g., a luminescent label).

A "polymerase" is an enzyme generally for joining 3'-OH 5'-triphosphate nucleotides, oligomers, and their analogs. Polymerases include, but are not limited to, template-dependent DNA-dependent DNA polymerases, DNA-dependent RNA polymerases, RNA-dependent DNA polymerases, and RNA-dependent RNA polymerases. Polymerases include but are not limited to T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Vent DNA polymerase (New England Biolabs), Deep Vent DNA polymerase (New England Biolabs), Bst DNA Polymerase Large Fragment, Stoeffel Fragment, 9° N DNA Polymerase, Pfu DNA Polymerase, Tfl DNA Polymerase, RepliPHI Phi29 Polymerase, Tli DNA polymerase, eukaryotic DNA polymerase beta, telomerase, Therminator polymerase (New England Biolabs), KOD HiFi DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. Nos. 6,329,178; 6,602,695; and 6,395,524 (incorporated by reference). These polymerases include wild-type, mutant isoforms, and genetically engineered variants.

A "DNA polymerase" is a polymerase that produces DNA from deoxynucleotide monomers (dNTPs). "Eubacterial DNA polymerase" as used herein refers to the Pol A type DNA polymerases (repair polymerases) from Eubacteria, including but not limited to DNA Polymerase I from *E. coli*, Taq DNA polymerase from *Thermus aquaticus* and DNA Pol I enzymes from other members of genus *Thermus*, and other eubacterial species etc.

As used herein, the term "target" refers to a nucleic acid species or nucleic acid sequence or structure to be detected or characterized.

Accordingly, as used herein, "non-target", e.g., as it is used to describe a nucleic acid such as a DNA, refers to nucleic acid that may be present in a reaction, that is not the subject of detection or characterization by the reaction. In some embodiments, non-target nucleic acid may refer to nucleic acid present in a sample that does not, e.g., contain a target sequence, while in some embodiments, non-target may refer to exogenous nucleic acid, i.e., nucleic acid that does not originate from a sample containing or suspected of containing a target nucleic acid, and that is added to a reaction, e.g., to normalize the activity of an enzyme (e.g., polymerase) to reduce variability in the performance of the enzyme in the reaction.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel.

As used herein, the term "flap assay reagents" or "invasive cleavage assay reagents" refers to all reagents that are required for performing a flap assay or invasive cleavage assay on a substrate. As is known in the art, flap assays generally include an invasive oligonucleotide, a flap oligonucleotide, a flap endonuclease and, optionally, a FRET cassette, as described above. Flap assay reagents may optionally contain a target to which the invasive oligonucleotide and flap oligonucleotide bind.

As used herein, the term "flap oligonucleotide" refers to an oligonucleotide cleavable in a detection assay, such as an invasive cleavage assay, by a flap endonuclease. In preferred embodiments, a flap oligonucleotide forms an invasive cleavage structure with other nucleic acids, e.g., a target nucleic acid and an invasive oligonucleotide.

DETAILED DESCRIPTION OF THE INVENTION

Provided herein is technology relating to the amplification-based detection of nucleic acids and particularly, but not exclusively, to methods and compositions for altering the behavior of calibration standards to mimic natural samples and minimize variability in the activity of manufactured polymerases, such as Taq polymerase, e.g., when using combined amplification and invasive cleavage assay reactions.

Typically, when a small change in a reagent produces a shift in a standard curve (e.g., a change in the slope and/or intercept), the shift may indicate a suboptimal condition relative to one or more components of the reaction. As such, the conventional practice is to optimize the assay components and their concentrations.

In the case of standard curves changing in response to changes in a source, manufacturer, or manufacturer's lot of Taq polymerase, it was initially suspected that slight lot-to-lot variations in the Taq concentration resulted in the detected differences in the standard curves. To test this hypothesis, the K-ras (KRAS) gene and a gene panel called "ANB," consisting of ACTB (β-actin, which typically serves as a reference standard in the assays), NDRG4 (member of the N-myc downregulated gene family), and BMP3 (bone morphogenetic protein 3), were quantified in a QuARTS reaction using Taq DNA polymerase from three different lots and at concentrations of 0.04, 0.06, 0.08, and 1 unit/μl. Surprisingly, the data collected (Table 1) show that adjusting the Taq concentration did not correct errors in quantifying the ANB and KRAS strands.

If the polymerases from different lots exhibited the same performance but varied only in concentration, one would expect that in the spiked samples, one would calculate out the same figures for the quantity of input DNA (number of strands) regardless of the lot of enzyme used, even if the gross fluorescence signals varied, and that the differences between lots could be addressed by adjusting the amount of enzyme added when switching between lots. Table 1 shows, however, that the differences in performance cannot be compensated for by adjusting enzyme concentration. Using higher or lower amounts of enzyme from one lot did not result in reaction performance matching the performance level of a different lot of the same enzyme. For example, the performance of 0.06 units of lot 11256007 is not the same as, or close to, the performance of 0.04, 0.06, 0.08, or 0.1 units of the other lots of Taq tested, demonstrating that the variable performance cannot be attributed to differences in the unit concentrations of the Taq DNA polymerase.

Accordingly, other solutions to this problem in variability are provided in the description of the present technology. In the following description, the section headings used herein are for organizational purposes only and are not to be construed as limiting the described subject matter in any way.

TABLE 1

| | | | Mean strands | | | | | | | | |
|---|---|---|---|---|---|---|---|---|---|---|---|
| | | | FAM Taq lot | | | HEX Taq lot | | | Quasar 670 Taq lot | | |
| Assay | SampleID | Taq U/ul | 11256007 | 31614211 | 32171002 | 11256007 | 31614211 | 32171002 | 11256007 | 31614211 | 32171002 |
| ANB | 200 strands per reaction spiked | 0.04 | 3,973 | 3,217 | 2,767 | 5,399 | 3,951 | 3,740 | 12,026 | 10,884 | 4,334 |
| | | 0.06 | 4,723 | 3,631 | 3,017 | 6,462 | 4,548 | 4,443 | 11,046 | 9,979 | 5,062 |
| | | 0.08 | 3,189 | 4,314 | 3,989 | 6,253 | 5,428 | 5,278 | 5,602 | 9,126 | 5,558 |
| | | 0.1 | 3,323 | 4,504 | 4,842 | 5,690 | 5,201 | 6,713 | 5,056 | 8,512 | 7,330 |
| Kras | sDNA | 0.04 | 32 | 9 | 13 | 19 | 0 | 19 | 7,041 | 3,729 | 7,144 |
| | | 0.06 | 9 | 9 | 6 | 3 | 9 | 7 | 12,895 | 5,917 | 11,801 |
| | | 0.08 | 4 | 25 | 0 | 1 | 16 | 0 | 12,506 | 8,122 | 14,937 |
| | | 0.1 | 4 | 15 | 0 | 1 | 8 | 0 | 10,519 | 9,949 | 9,101 |
| | 200 strands per reaction spiked | 0.04 | 541 | 371 | 525 | 1,056 | 722 | 1,335 | 7,499 | 4,350 | 7,678 |
| | | 0.06 | 789 | 441 | 679 | 1,746 | 1,232 | 1,564 | 12,173 | 7,060 | 14,226 |
| | | 0.08 | 578 | 1,046 | 218 | 2,705 | 2,051 | 1,300 | 12,315 | 10,831 | 17,599 |
| | | 0.1 | 358 | 1,166 | 88 | 2,322 | 1,927 | 434 | 12,660 | 13,722 | 10,327 |

In the table above, for ANB assays (see left column), the FAM signal indicates the NDRG4 target, HEX indicates the BMP3 target, and Quasar 670 indicates the ACTB target; for the Kras assays, the FAM signal indicates KRAS 35T, 34T, 38 targets, HEX indicates KRAS 35A, 35C, 34A 34C targets, and Quasar 670 indicates ACTB targets. These data are averaged signals from duplicate reactions for normal stool DNA ("sDNA") samples, and triplicate reactions for the samples in which plasmid DNA was spiked into sDNA. The amount of normal stool DNA used is 10 μl of a preparation such as would typically be produced by DNA capture from a stool sample for testing, e.g., using a QuARTS assay.

The data in Table 1 shows that there is notable variation in the signal generated by the use of the same unit amounts of different lots of the Taq DNA polymerase. Each row in Table 1 is associated with a particular number of units of Taq DNA polymerase per reaction, but using different lots of Taq shows that different lots produced highly variable signals from the same input target DNA. For example, when 0.04 u/μl was used in the ANB assay, the signal in the Quasar 670 channel showed more than twice as much signal from lots 11256007 and 316142211 as from lot 32171002.

Embodiments of the Technology

1. Methods to Minimize DNA Polymerase Variability

Provided herein is technology related to minimizing polymerase variability by adding extraneous, non-target DNA to samples. While the technology is described herein in particular aspects as it relates to PCR-invasive cleavage assays, such as QuARTS assay technology, the technology is not limited in its application to PCR-invasive cleavage assays and QuARTS assays, but finds use in any technology in which a polymerase is employed. Indeed, it is contemplated that the technology finds use in any test, assay, or other technology in which an enzyme contacts a nucleic acid, and, in particular, in any test, assay, or other technology in which an enzyme contacts a nucleic acid according to a degree of sequence specificity to differentiate target from background. Examples of such technologies are ligases, restriction enzymes, DNA polymerases, RNA polymerases, reverse transcriptases, telomerases, recombinases, DNA and/or RNA editing enzymes, RNA splicing enzymes, methylases, enzymes for poly-A tail addition, nucleases, miRNA and siRNA processing enzymes, and the like.

While not limiting the invention to any particular mechanism of action, it has been observed that the presence of hairpin oligonucleotides (e.g., hairpin FRET cassettes as used, for example, in some embodiments of invasive cleavage detection assays) may have an inhibiting effect on DNA polymerase present in the same vessel, as assessed by sample and signal amplification. See, e.g., U.S. Patent Publication 2006/0147955 to Allawi, which is incorporated herein by reference for all purposes. Allawi et al. observed that when PCR and invasive cleavage assay components were combined, the hairpin FRET oligonucleotides affected polymerase performance. As such, the present technology finds application in DNA polymerase-based assays conducted in the presence of hairpin-containing DNAs, including but not limited to PCR-invasive cleavage assays, such as QuARTS assays.

According to the technology, purified exogenous non-target DNA is added to samples before and/or while contacting the samples with an enzyme such as a polymerase. The non-target DNA is added to the sample or reaction mixture, for example, at a concentration of approximately 2 to 20 ng per μl of reaction mixture, preferably approximately 6 to approximately 7 ng per μl of reaction mixture, when approximately 0.01 to 1.0 U/μl of enzyme, e.g., 0.05 U/μl of enzyme (e.g., a polymerase such as, e.g., Taq polymerase) is used in the assay. It is contemplated that a amounts of from 10 ng to 1 μg of the purified exogenous non-target DNA are added depending on the particular assay system, for example, when considering the particular enzyme and enzyme concentrations, concentrations of other assay components (e.g., primers, salts, target, etc.) present, and relevant physical and chemical factors such as temperature, pressure, water activity, volume, presence of inhibitors, etc.

2. Compositions for Minimizing Polymerase Variability

In another aspect, compositions according to the technology comprise non-target DNA, and, in some embodiments, one or more of a buffer, one or more salts, a preservative (e.g., sodium azide), a chelator (EDTA, EGTA, BAPTA, etc.), a free radical scavenger, etc., typically in an aqueous solution. However, non-aqueous and/or organic solutions (e.g., dimethyl sulfate) are also contemplated as are dried compositions provided, e.g., as a powder (e.g., freeze-dried, lyophilized, etc.). The technology includes embodiments of compositions comprising the non-target DNA as a composition to add to an assay sample (e.g., a composition comprising non-target DNA before it has been added to a sample) and embodiments of compositions comprising the non-target DNA and the components of the assay sample (e.g., after addition of the non-target DNA to the sample).

It is contemplated that the technology encompasses the use of DNA from any source. Specific examples of the technology provided herein relate to the use of fish (e.g., herring) DNA and/or mammalian (e.g., mouse) DNA. However, in some embodiments, the non-target nucleic acid is isolated from another source, e.g., a natural source (e.g., an animal, a bacterium, an archaeon, a virus, a eukaryote (e.g., a yeast), a plant, a pool or mixture of one or more of these, etc., as taken from an environmental or biological sample, from a culture, from a recombinant source, or a mixture of one or more of these) or, in some embodiments, the nucleic acid is synthetic (e.g., produced chemically (e.g., by a machine) and optionally comprises one or more sequences present in a natural source and/or random sequences). In some embodiments, the sequence of the non-target nucleic acid is known and in some embodiments the sequence of the non-target nucleic acid is not known or is partially known. In some embodiments, the non-target nucleic acid is labeled or tagged such that it can be distinguished or isolated from target nucleic acid or from assay sample nucleic acid that is not the added non-target nucleic acid. In some embodiments, the non-target nucleic acid is modified such that it is not a substrate for the assay to which the non-target nucleic acid is added. For example, non-target DNA with a blocked 3' end is not a substrate for primer extension by a polymerase. In addition, in some embodiments, certain modifications of the bases of a non-target nucleic acid inhibit the binding of a primer, thus inhibiting the non-target nucleic acid from acting as a template. In some embodiments, the non-target nucleic acid is susceptible to digestion and/or transformation to a state that does not interfere with the downstream processing of a sample.

The extent of purification of the non-target nucleic acid varies. In some embodiments, the non-target nucleic acid is DNA substantially or essentially free of RNA and in some embodiments the non-target nucleic acid is RNA substantially free or essentially free of DNA. In some embodiments the non-target nucleic acid is substantially or essentially free of proteins. In specific embodiments, the nucleic acid is substantially free of enzymes that degrade a nucleic acid and/or that inhibit and/or deleteriously affect an assay of a sample to which the non-target nucleic acid is added. Similarly, some embodiments include compositions are essentially free of a component such as, e.g., an ion, a salt, a lipid, or some other component that results in the degradation or sequestration of DNA and/or that inhibits an assay for the detection of the target nucleic acid.

In some embodiments, compositions comprise an aqueous buffer medium that is optimized for the particular non-target DNA and/or polymerase in the assay in which the non-target DNA is to be used. Buffer systems include citrate buffers, acetate buffers, borate buffers, and phosphate buffers. Other exemplary buffers include citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate and benzoic acid. Preferred exemplary buffering agents that are present in embodiments of compositions according to the technology described include Tris, Tricine, HEPES, MOPS, and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, e.g., a pH of approximately 8.0.

In some embodiments, the compositions include a source of monovalent ions and/or a source of divalent cations. Any convenient source of monovalent ions, such as potassium chloride, sodium chloride, potassium acetate, sodium acetate, potassium glutamate, ammonium chloride, ammonium sulfate, and the like may be employed. Divalent ions are, e.g., magnesium, manganese, calcium, etc.

In some embodiments, the compositions comprise one or more chelating agents, such as ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include EGTA, BAPTA, citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof, sodium desoxycholate and derivatives thereof.

In some embodiments, the compositions comprise an antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the compositions comprise a cryoprotectant. Common cryoprotecting agents include histidine, polyethylene glycol, polyvinyl pyrrolidine, lactose, sucrose, mannitol, and polyols. Accordingly, in some embodiments, compositions are stored frozen.

In some embodiments, the compositions comprise a preservative. Common preservatives include chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like. In some embodiments, compositions comprise sodium azide ($NaN_3$), e.g., at a concentration of approximately 0.025%.

Compositions are prepared in some embodiments as concentrated solutions, e.g., as a 2×, 5×, 10×, 20×, 25×, 50×, 100×, or more concentrated, solution. As an example, a 2× solution is added to an equal part of another solution to provide the non-target DNA at the final concentration at which it is used (e.g., at 1×). For a working concentration of 200 ng of non-target DNA per 20 µl reaction sample, a 2× concentrated solution is prepared to comprise 400 ng/20 µl, or 20 ng/µl non-target DNA. For this same reaction volume, a 10× solution is prepared at 2000 ng per 20 µl, or at 100 ng/µl, etc. Some embodiments provide that compositions are protected from light and/or ionizing radiation.

3. Uses

In some embodiments, the methods and compositions provided herein find use in an assay for detecting and/or quantifying a nucleic acid. For example, the technology finds use in assays based, for example, on PCR, INVADER assay, PCR-invasive cleavage assays and/or QuARTS assay methods. In particular, the technology finds use in quantitative assays in which standards are used to construct a standard curve.

3.1. Use in QuARTS Assay

In some embodiments, the technology finds use to normalize enzyme (e.g., polymerase) activity to reduce enzyme-associated variability in a QuARTS assay. The QuARTS assay is often used to quantify the number of copies of a particular DNA in a sample. The QuARTS technology combines a polymerase-based target DNA amplification process with an invasive cleavage-based signal amplification process. Fluorescence signal generated by the QuARTS reaction is monitored in a fashion similar to real-time PCR. During each amplification cycle, three sequential chemical reactions occur in each assay well, with the first and second reactions occurring on target DNA templates and the third occurring on a synthetic DNA target labeled with a fluorophore and quencher dyes, thus forming a fluorescence resonance energy transfer (FRET) donor and acceptor pair. The first reaction produces amplified target with a polymerase and oligonucleotide primers, and the second reaction uses a highly structure-specific 5'-flap endonuclease-1 (FEN-1) enzyme reaction to release a 5'-flap sequence from a target-specific oligonucleotide probe that binds to the product of the polymerase reaction, forming an overlap flap substrate. In the third reaction, the cleaved flap binds to a specially designed oligonucleotide containing a fluorophore and quencher closely linked in a FRET pair such that the fluorescence is quenched (FRET cassette). The released probe flap hybridizes in a manner that forms an overlap flap substrate that allows the FEN-1 enzyme to cleave the 5'-flap containing the fluorophore, thus releasing it from the quencher molecule. The released fluorophore generates fluorescence signal to be detected. During the second and third reactions, the FEN-1 reaction can cut multiple probes per target, generating multiple 5'-flaps and multiple FRET cassettes per cleaved 5'-flap, giving rise to additional linear signal amplification to the overall reaction.

In some applications, the assay is designed for methylated DNA analysis. In some configurations, each assay is designed to detect multiple genes, e.g., 3 genes reporting to 3 distinct fluorescent dyes. See, e.g., Zou, et al., (2012) "Quantification of Methylated Markers with a Multiplex Methylation-Specific Technology", *Clinical Chemistry* 58: 2, incorporated herein by reference for all purposes.

An exemplary QuARTS reaction typically comprises approximately 400-600 nmol/l (e.g., 500 nmol/l) of each primer and detection probe, approximately 100 nmol/l of the invasive oligonucleotide, approximately 600-700 nmol/l of each FAM (e.g., as supplied commercially by Hologic), HEX (e.g., as supplied commercially by BioSearch Technologies, IDT), and Quasar 670 (e.g., as supplied commercially by BioSearch Technologies) FRET cassettes, 6.675 ng/µl FEN-1 (e.g., Cleavase® (e.g., 2.0), Hologic, Inc.), 1 unit Taq DNA polymerase in a 30 µl reaction volume (e.g., GoTaq® DNA polymerase, Promega Corp., Madison, Wis.), 10 mmol/l 3-(n-morpholino)propanesulfonic acid (MOPS), 7.5 mmol/l $MgCl_2$, and 250 µmol/l of each dNTP. Exemplary QuARTS cycling conditions consist of an initial incubation at 95° C. for 3 minutes, followed by 10 cycles of 95° C. for 20 seconds, 67° C. for 30 seconds, and 70° C. for 30 seconds. After completion of the 10 cycles, an additional 37 cycles at 95° C. for 20 seconds, 53° C. for 1 minute, 70° C. for 30 seconds, and 40° C. for 30 seconds are typically performed. In some applications, analysis of the quantification cycle ($C_q$) provides a measure of the initial number of target DNA strands (e.g., copy number) in the sample.

The technology of the present invention finds use in normalizing the activity and reducing variability in the performance of polymerases, e.g., that are used in a QuARTS assay, for example, by use of the methods and compositions described herein. These embodiments are further understood by the illustrative examples provided below.

EXPERIMENTAL EXAMPLES

Example 1

During the development of embodiments of the technology provided herein, it was hypothesized that the addition of exogenous non-target containing DNA would minimize manufacturing variability in Taq polymerase and/or resemble the non-target DNA that is present in some complex samples such as stool DNA (sDNA) samples that are often used for colorectal cancer screening. To test this hypothesis, varying amounts of mouse and herring DNA were added to KRAS calibrators at 10, 100, 1000 and 10,000 copies per reaction (n=4 replicates each). Then, using two different lots of Taq polymerase (designated "DEV" and "New Pro"), the differences between the standard curves' slopes and intercepts were examined. Concentrations of the reaction components (in nM, except as indicated for dNTPs) are shown below:

| KRAS Reverse primer | 300 | KRAS 35C probe | 500 |
| ACTB Reverse primer | 500 | KRAS 34A probe | 500 |
| KRAS 34A forward primer | 250 | KRAS 34C probe | 500 |

-continued

| | | | |
|---|---|---|---|
| KRAS 34T forward primer | 250 | KRAS 35T probe | 500 |
| KRAS 34C forward primer | 250 | KRAS 34T probe | 500 |
| KRAS 35A forward primer | 250 | KRAS 38A probe | 250 |
| KRAS 35T forward primer | 250 | ACTB probe | 500 |
| KRAS 35C forward primer | 250 | A5 HEX FRET | 100 |
| KRAS 38A forward primer | 250 | A7 FAM FRET | 100 |
| ACTB WT forward primer | 500 | A1 Quasar670 FRET | 150 |
| KRAS 35A probe | 500 | 25 mM dNTPs | 250 (uM) |

Reaction volume = 30 μl,

Dye Reporting:

KRAS 35A, 35C, 34A 34C=HEX

KRAS 35T, 34T, 38A=FAM

ACTB=Quasar

The cycling parameters for these QuARTS reactions are follows:

| Stage | Temp (° C.) | Time (minutes) | Ramp Rate | Number of |
|---|---|---|---|---|
| Pre-Incubation | 95 | 3:00 | 100% | 1 |
| Amplification 1 | 95 | 0:20 | 100% | 10 |
| | 63 | 0:30 | 100% | |
| | 70 | 0:30 | 100% | |
| Amplification 2 | 95 | 0:20 | 100% | 35 |
| | 53 | 1:00 | 100% | |
| | 70 | 0:30 | 100% | |
| Cooling | 40 | 0:30 | 100% | 1 |

Figure 2A:
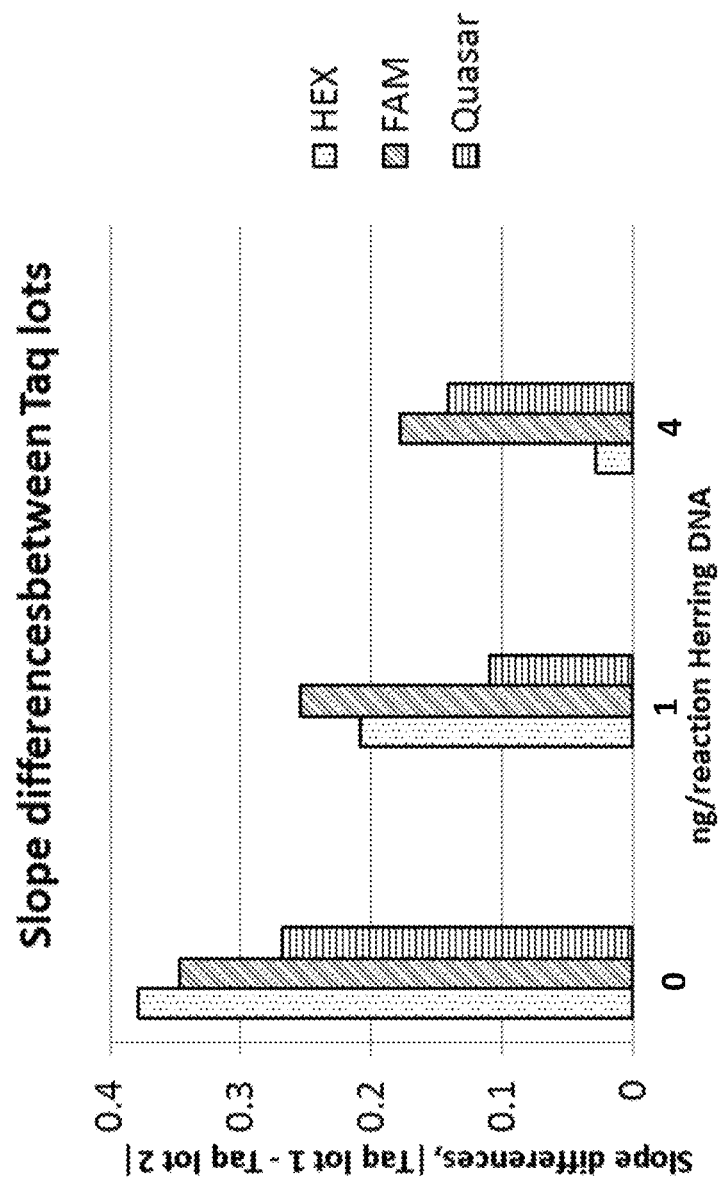
FIGS. 2A and 2B are plots showing that addition of herring DNA decreases the differences between the slopes and intercepts among samples analyzed with two different lots of Taq polymerase in a QuARTS assay. The reactions had 0, 1 or 4 ng of herring DNA per 30 µl reaction.
Figure 2B:
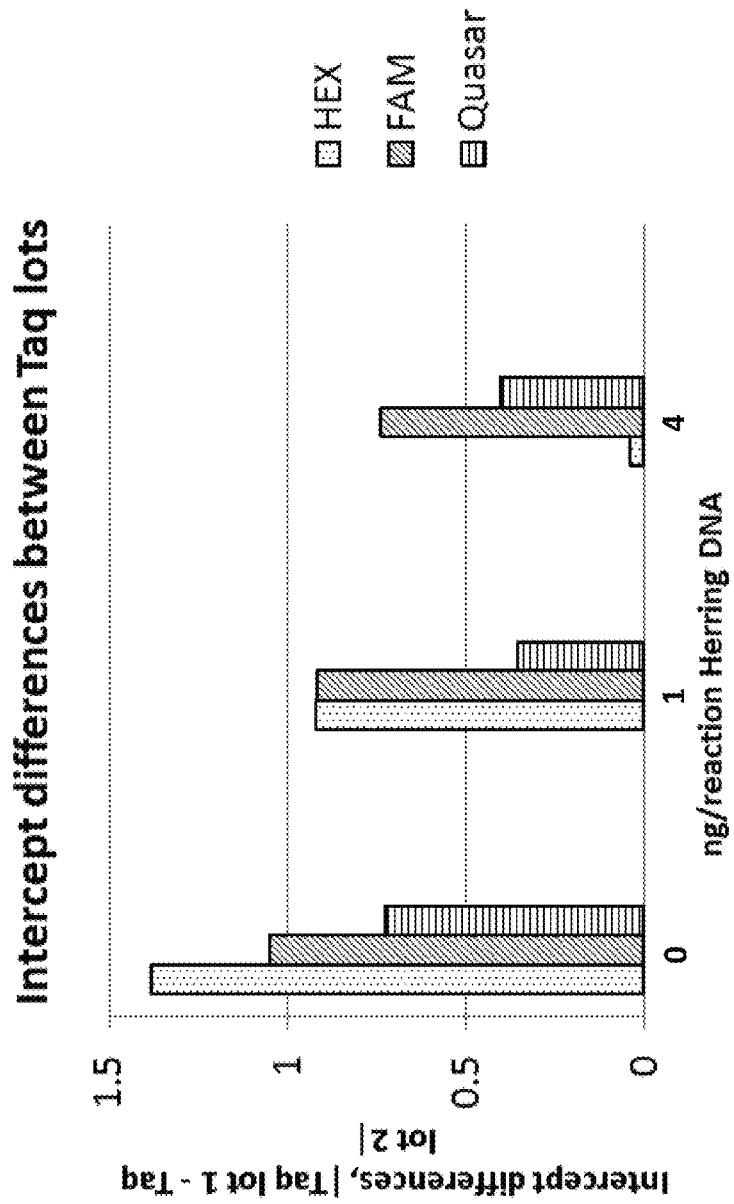

Results are shown in FIGS. 2A and 2B. These data show that addition of herring DNA decreases the differences between the slopes (FIG. 2A) and intercepts (FIG. 2B) of the signal from the calibrators, and that as the amount of herring DNA is increased from 1 to 4 ng/reaction, the differences between the slopes and intercepts decrease. Mouse DNA had the same effect (data not shown).

Figure 3A:
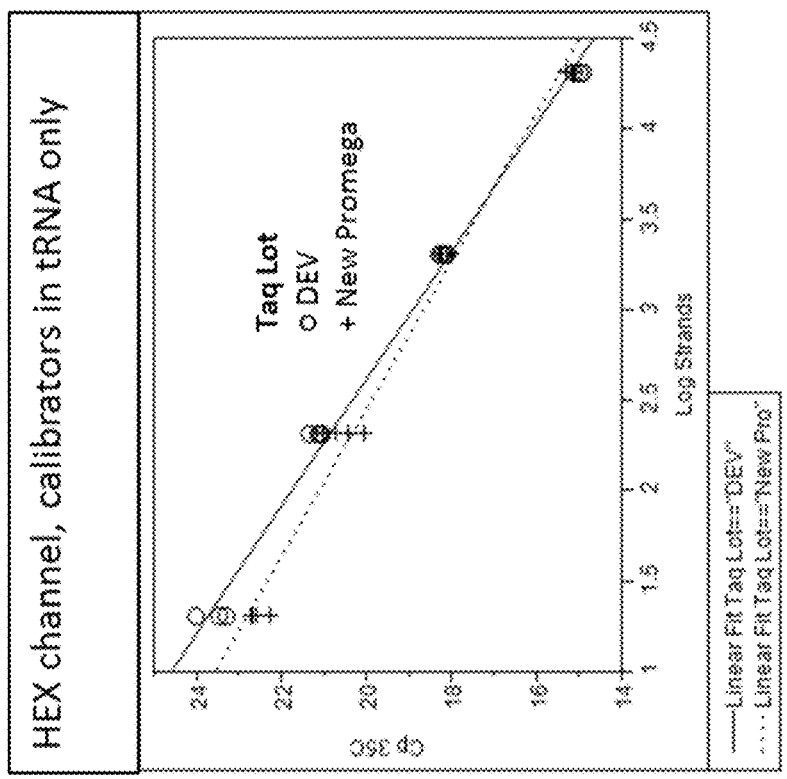
FIGS. 3A and 3B are plots comparing the effect of adding tRNA (FIG. 3A) to the effect of adding herring DNA (FIG. 3B) on the linear log fit of data from sets calibration reactions performed using two different lots of Taq DNA polymerase.
Figure 3B:
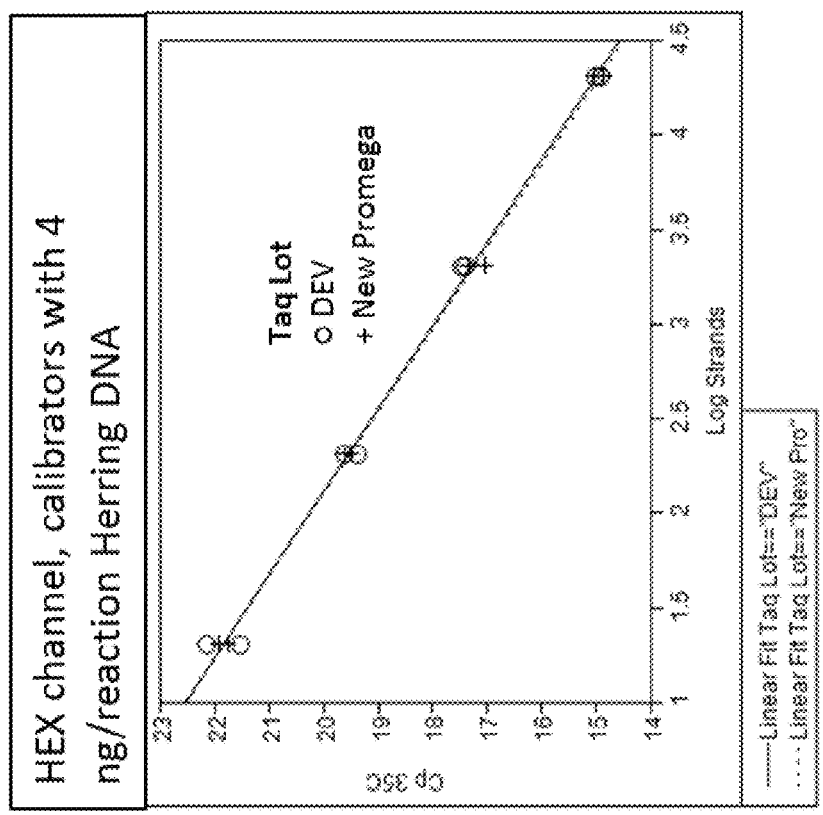
Figure 4A:
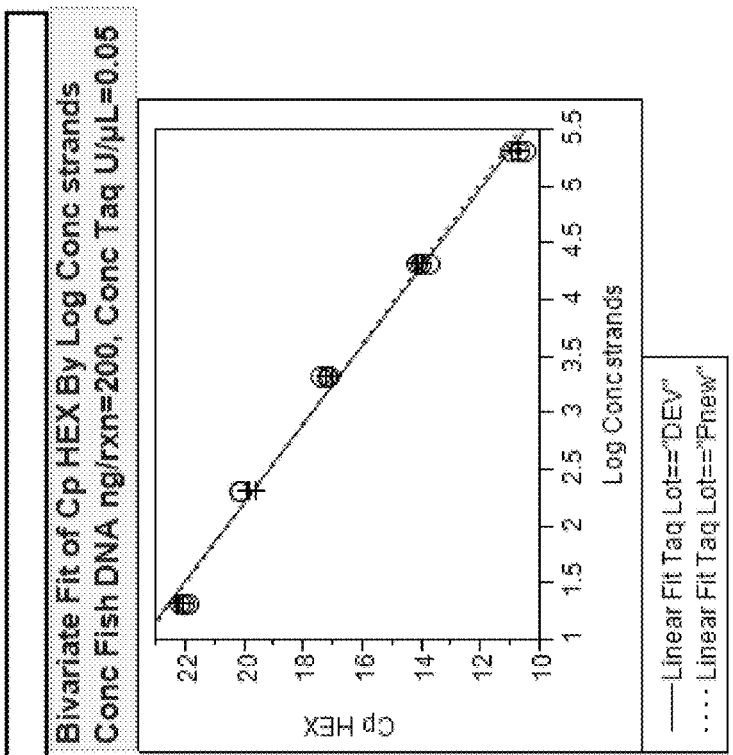
FIGS. 4A-4F are a series of plots showing that the addition of 200 ng of fish DNA per 30 µl reaction produced nearly identical plots using two different lots of Taq DNA polymerase "DEV" and "Pnew". The different lots of Taq polymerase were tested at 0.05 u/µl of reaction volume (4A, 4B and 4C) and 0.07 units/µl of reaction volume (4D, 4E, and 4F), in QuARTS assays as described below.
Figure 4B:
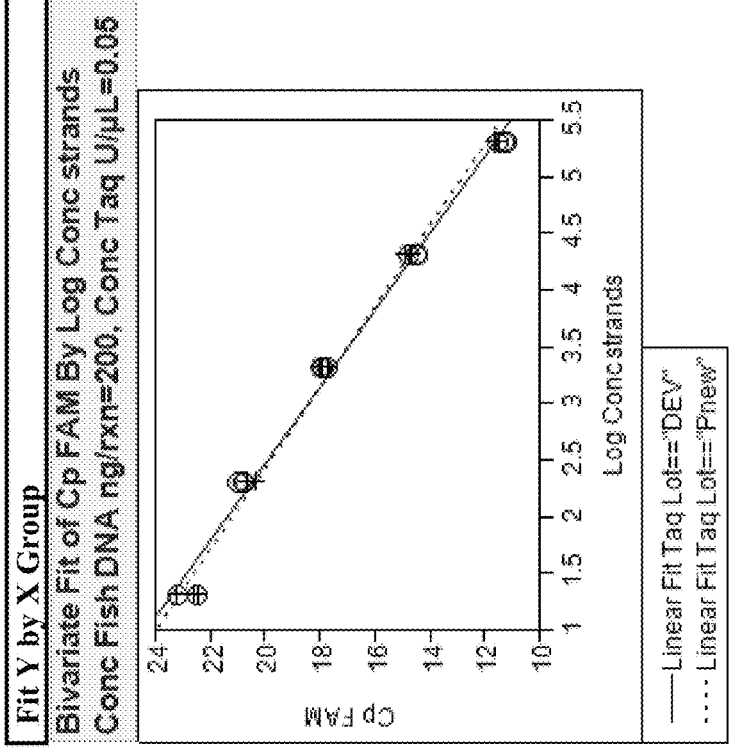
Figure 4D:
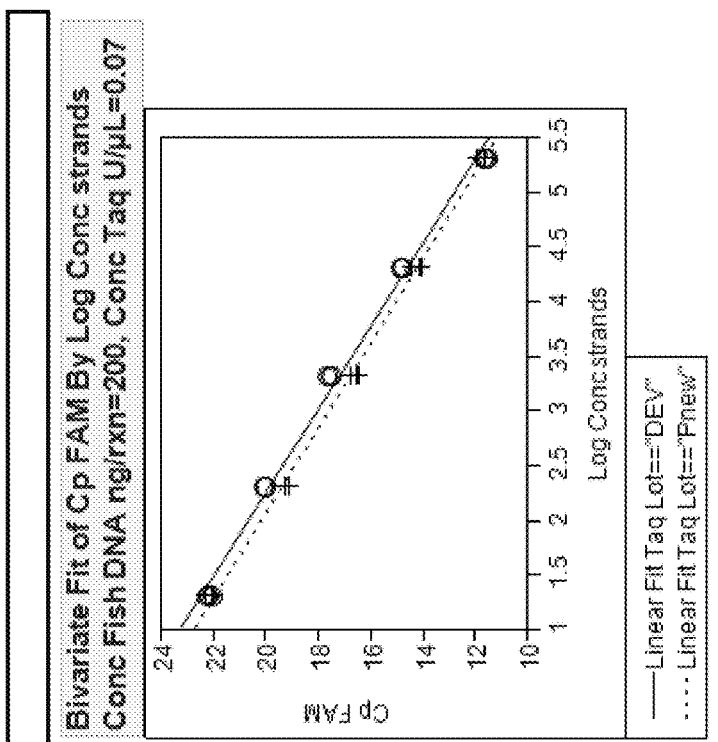
Figure 4C:
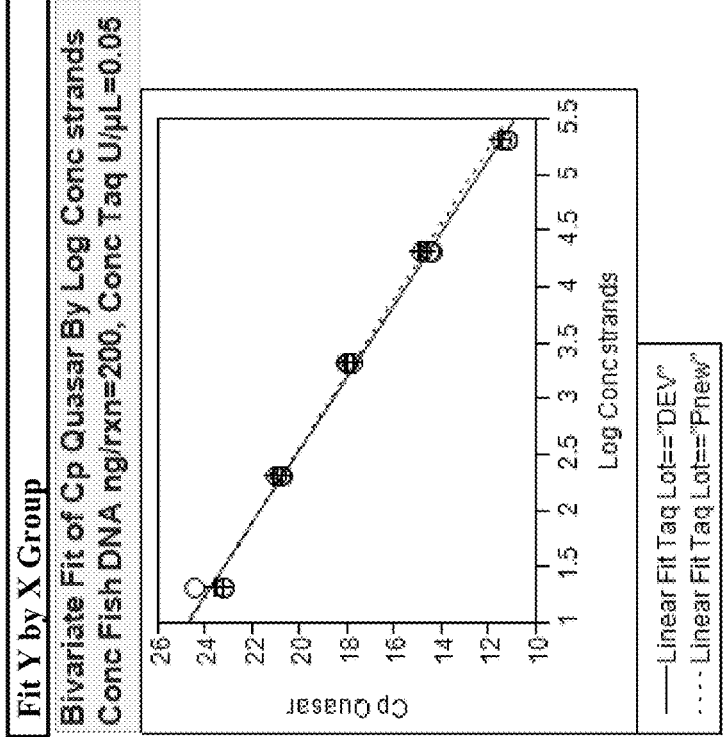
Figure 4E:
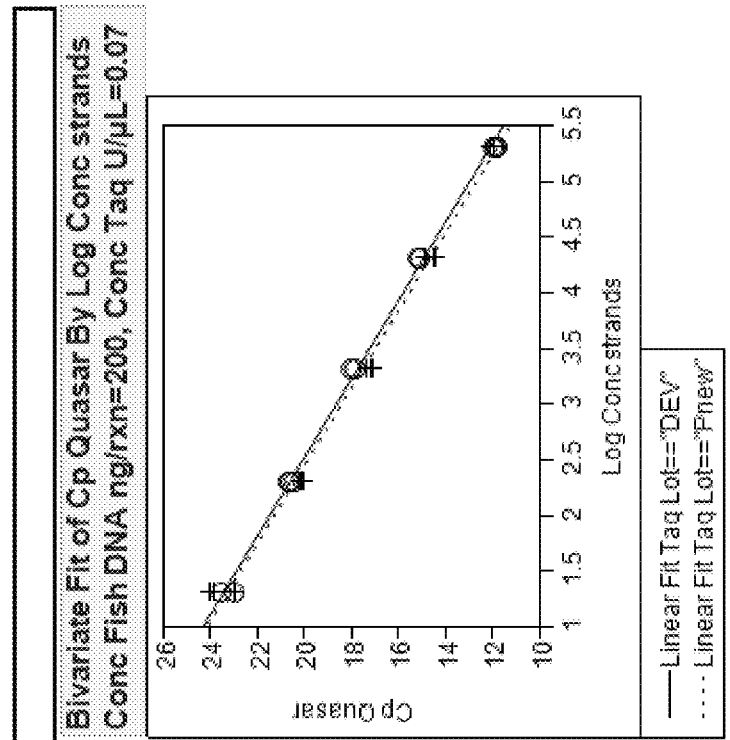
Figure 4F:
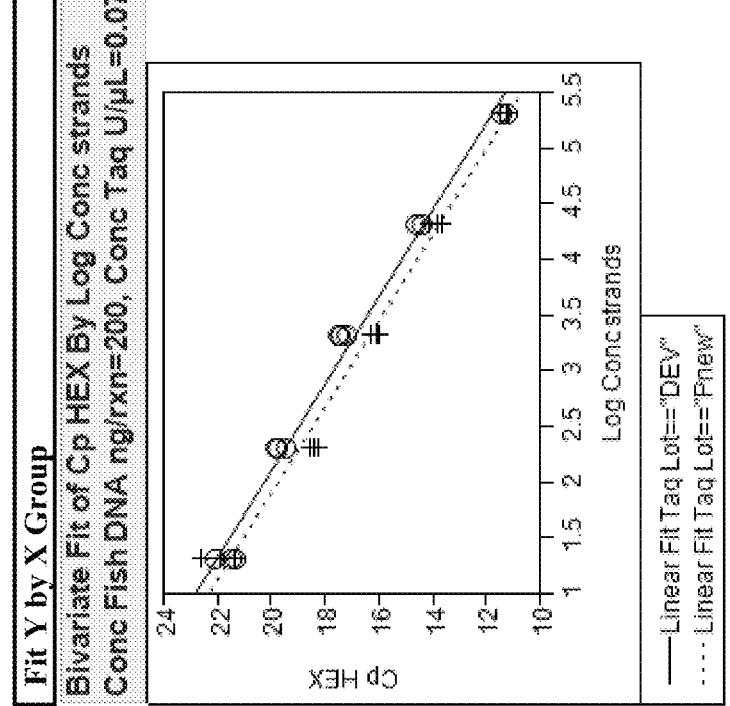

Example 2 tRNA is often added to calibrator samples used in quantitative PCR, e.g., to minimize sticking of calibrator DNA to vessels. To test whether tRNA had the same effect on polymerase performance in a PCR-invasive cleavage assay as observed with herring DNA, QuARTS reactions were conducted as described above, but in the presence of 20 ng/μl of tRNA instead of 4 ng/μl of herring DNA. The results are shown in FIG. 3. Calibration plots for the two lots of Taq are nearly identical in the presence of herring DNA (FIG. 3B), but not in the presence of tRNA (FIG. 3A), indicating that the performance variation is not due to binding of the calibrator DNA to the vessels.

Example 3

During the development of embodiments of the technology, data were collected from experiments in which standard curves were generated from different lots of Taq in the presence of USB/Affymetrix fish (salmon) DNA (Cleveland, Ohio). A comparison of two lots of Promega "Hot Start Go Taq" (indicated as "DEV" and "Pnew", and present at concentrations of 0.03, 0.05, and 0.07 U/μl; Promega Corp., Madison, Wis.) in the KRAS QuARTS assay with the addition of 200 ng/reaction of USB/Affymetrix fish DNA showed that the standard curves were nearly identical between the two Taq lots for all three dyes (Table 3). FIG. 4 shows plots of the data from the 0.05 and 0.07 U/μl reaction sets.

TABLE 3

| | | delta Cp, DEV lot Taq – Pr new lot Taq | | | | | | | |
|---|---|---|---|---|---|---|---|---|---|
| | | Taq concentration 0.03 U/μL | | | Taq concentration 0.05 U/μL | | | Taq concentration 0.07 U/μL | | |
| | Target | FAM | HEX | Quasar 670 | FAM | HEX | Quasar 670 | FAM | HEX | Quasar 670 |
| KRAS | 1e1 cp/rxn | −0.58 | −0.05 | −0.26 | 0.17 | −0.17 | 0.11 | 0.01 | −0.38 | −0.28 |
| Calibrator: | 1e2 cp/rxn | −0.01 | −0.11 | −0.05 | 0.36 | 0.32 | −0.13 | 0.75 | 1.22 | 0.41 |
| 38A, 35C, | 1e3 cp/rxn | −0.20 | −0.29 | −0.20 | −0.06 | 0.02 | −0.06 | 0.94 | 1.2 | 0.78 |
| ACTB WT | 1e4 cp/rxn | −0.17 | −0.26 | −0.17 | −0.30 | −0.18 | −0.28 | 0.57 | 0.68 | 0.45 |
| | 1e5 cp/rxn | −0.13 | −0.22 | −0.26 | −0.26 | −0.20 | −0.28 | −0.16 | 0.03 | −0.14 |
| Controls | KRAS WT 1e5 | 0.13 | 0.00 | 0.00 | 0.62 | 0.51 | 0.00 | 0.06 | 0.43 | 0 |
| | NTC | NA | NA | NA | NA | NA | NA | NA | NA | NA |
| Average difference in Cp values, DEV – Pr new Taq lots | | −0.16 | −0.15 | −0.16 | 0.09 | 0.05 | −0.11 | 0.36 | 0.53 | 0.20 |

A comparison of Roche fish (cod and herring sperm) DNA (Roche Applied Science, Mannheim, Germany) and USB/Affymetrix fish (salmon) DNA at 200 ng/reaction with 0.05 U/μl of Taq DNA polymerase result in nearly identical signals for KRAS samples across the two different Taq lots (Table 4).

TABLE 4

| Sample Name | Fish DNA Supplier | Taq Lot | Strands FAM Mean | Strands HEX Mean | Strands Quasar Mean | Strands FAM CV | Strands HEX CV | Strands Quasar CV | N |
|---|---|---|---|---|---|---|---|---|---|
| sDNA | Roche | DEV | 7.94 | 5.76 | 10238.66 | 15.88 | 40.85 | 9.31 | 4.00 |
| | | Pr New | 8.90 | 6.04 | 9269.49 | 7.03 | 83.68 | 7.89 | 2.00 |
| | USB | DEV | 8.03 | 6.29 | 9169.32 | 32.00 | 40.99 | 7.64 | 4.00 |
| | | Pr New | 10.68 | 8.21 | 9506.81 | 22.78 | 58.11 | 5.08 | 2.00 |

TABLE 4-continued

| Sample Name | Fish DNA Supplier | Taq Lot | Strands FAM Mean | Strands HEX Mean | Strands Quasar Mean | Strands FAM CV | Strands HEX CV | Strands Quasar CV | N |
|---|---|---|---|---|---|---|---|---|---|
| sDNA + 1e2 | Roche | DEV | 551.87 | 540.18 | 10337.09 | 2.27 | 2.76 | 10.66 | 2.00 |
| | | Pr New | 448.16 | 475.11 | 10013.05 | 19.87 | 19.28 | 15.70 | 4.00 |
| | USB | DEV | 491.86 | 535.89 | 9250.39 | 19.48 | 5.49 | 4.53 | 2.00 |
| | | Pr New | 469.66 | 571.85 | 10210.97 | 21.11 | 14.41 | 15.08 | 4.00 |

Example 4

During the development of embodiments of the technology, tests were conducted to assess if including fish DNA in samples affects the detection of targets in the assay. In particular, a QuARTS reaction to quantify the ANB panel was performed using 0.05 and 0.07 U/μl Taq polymerase in the presence of 200 ng Roche fish DNA per reaction. The tests quantified the ANB panel in stool DNA and stool DNA spiked with 100 copies of ANB borne on a plasmid. Results show no change in the calibrators or sample recoveries (Table 5). NTC=no-template negative control.

TABLE 5

| | | | | Mean | | | CV | | | |
|---|---|---|---|---|---|---|---|---|---|---|
| Sample Name | Taq Lot | Taq Conc | fish DNA | Strands FAM | Strands HEX | Strands Quasar | Strands FAM | Strands HEX | Strands Quasar | N |
| NTC | Dev | 0.05 | 0 | 0 | 0 | 0 | Missing | Missing | Missing | 8 |
| | | | 200 | 0 | 0 | 0 | Missing | Missing | Missing | 8 |
| | | 0.07 | 0 | 0 | 0 | 0 | Missing | Missing | Missing | 8 |
| | | | 200 | 0 | 0 | 0 | Missing | Missing | Missing | 8 |
| | Pr New | 0.05 | 200 | 0 | 0 | 0 | Missing | Missing | Missing | 8 |
| sDNA | Dev | 0.05 | 0 | 26 | 13 | 2020 | 28.04 | 3.22 | 3.99 | 2 |
| | | | 200 | 19 | 5 | 1785 | 12.10 | 41.70 | 6.60 | 2 |
| | | 0.07 | 0 | 39 | 16 | 2100 | 1.01 | 44.62 | 0.16 | 2 |
| | | | 200 | 36 | 36 | 2023 | 21.11 | 5.15 | 0.57 | 2 |
| | Pr New | 0.05 | 200 | 19 | 20 | 1964 | 61.37 | 44.10 | 4.75 | 2 |
| sDNA + 1e2 | Dev | 0.05 | 0 | 326 | 335 | 2120 | 13.76 | 18.95 | 3.05 | 2 |
| | | | 200 | 323 | 329 | 2119 | 5.27 | 8.46 | 3.88 | 2 |
| | | 0.07 | 0 | 399 | 364 | 2491 | 0.35 | 4.03 | 6.19 | 2 |
| | | | 200 | 343 | 387 | 2176 | 15.33 | 11.98 | 15.31 | 2 |
| | Pr New | 0.05 | 200 | 400 | 407 | 2277 | 3.99 | 8.77 | 3.62 | 2 |

The results indicate that including fish DNA in the dilution buffer of standards or calibrator samples reduces the variations in standard curves that result from variability in the performance of different production lots of Taq DNA polymerase. Additional experiments showed that this result was not achievable by adding tRNA alone, by using Taq from different vendors (data not shown), or by titrating the amount of Taq per reaction.

All publications and patents mentioned in the above specification are herein incorporated by reference in their entireties for all purposes. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

We claim:

1. A reaction mixture comprising:
   a) an amount of human genomic target nucleic acid;
   b) purified exogenous non-target DNA isolated from fish at a concentration of approximately 2 to 20 nanograms per μl of reaction mixture; and
   c) PCR amplification assay reagents comprising:
      i) thermostable DNA polymerase;
      ii) dNTPs;
      iii) a first primer and a second primer configured for amplifying a DNA product from said target nucleic acid;
      iv) an oligonucleotide with a fluorescent label; and
      v) a flap endonuclease,
      wherein said reaction mixture is characterized in that it can amplify said DNA product from said target nucleic acid and produce an amount of amplified DNA product proportional to the amount of said target nucleic acid in said reaction mixture.

2. The reaction mixture of claim 1, wherein said purified exogenous non-target DNA isolated from fish comprises DNA isolated from herring and/or cod and/or salmon.

3. The reaction mixture of claim 1, wherein said reaction mixture comprises purified exogenous non-target DNA isolated from fish at a concentration of approximately 6 to 7 nanograms per μl of reaction mixture.

4. The reaction mixture of claim 1, wherein said thermostable DNA polymerase is a eubacterial DNA polymerase.

5. The reaction mixture of claim 4, wherein said thermostable DNA polymerase is from *Thermus aquaticus*.

6. The reaction mixture of claim 1, wherein the DNA polymerase is modified for hot start PCR.

7. The reaction mixture of claim 1, wherein said flap endonuclease is a FEN-1 endonuclease.

* * * * *